United States Patent
Zhu et al.

(10) Patent No.: US 11,420,939 B2
(45) Date of Patent: Aug. 23, 2022

(54) METHOD FOR PREPARING ADRENOCHROME BY CATALYTIC OXIDATION USING NITROGEN-DOPED CARBON NANOTUBES

(71) Applicant: PEKING UNIVERSITY, Beijing (CN)

(72) Inventors: DongQiang Zhu, Beijing (CN); LangSha Yi, Beijing (CN); ChenHui Wei, Beijing (CN)

(73) Assignee: PEKING UNIVERSITY, Beijing (CN)

( * ) Notice: Subject to any disclaimer, the term of this patent is extended or adjusted under 35 U.S.C. 154(b) by 205 days.

(21) Appl. No.: 16/828,038

(22) Filed: Mar. 24, 2020

(65) Prior Publication Data

US 2021/0253526 A1    Aug. 19, 2021

(30) Foreign Application Priority Data

Feb. 18, 2020 (CN) .......................... 202010098106.5

(51) Int. Cl.
```
C07D 209/36    (2006.01)
B01D 15/12     (2006.01)
B01D 15/42     (2006.01)
B01D 9/04      (2006.01)
B01J 27/24     (2006.01)
B01J 25/02     (2006.01)
B01J 21/18     (2006.01)
B01J 35/02     (2006.01)
```
(52) U.S. Cl.
CPC ............ *C07D 209/36* (2013.01); *B01D 9/04* (2013.01); *B01D 15/125* (2013.01); *B01D 15/426* (2013.01); *B01J 21/185* (2013.01); *B01J 35/026* (2013.01)

(58) Field of Classification Search
CPC .. C07D 209/36; B01D 9/0013; B01D 15/426; B01D 15/125; B01D 15/12; B01D 15/42; B01D 9/04; B01J 27/24; B01J 21/185; B01J 35/026; B01J 35/02; B01J 21/18
See application file for complete search history.

(56) References Cited

PUBLICATIONS

Zhang et al., 1998, caplus an 1998:379334.*
Liu et al., 2010, caplus an 210:1342215.*
Tanabe, 1984, caplus an 1984:174661.*

* cited by examiner

*Primary Examiner* — Sun Jae Yoo
(74) *Attorney, Agent, or Firm* — Juan Carlos A. Marquez; Marquez IP Law Office, PLLC

(57) ABSTRACT

Disclosed is a method for preparing adrenochrome by catalytic oxidation using nitrogen-doped carbon nanotubes. The method catalyzes dissolved oxygen in an aqueous solution by the nitrogen-doped carbon nanotubes to rapidly oxidize adrenaline, which is completely transformed into adrenochrome. It is a novel preparation process of adrenochrome, which is simple, and has mild reaction conditions, high product purity, an impurity content less than $10^{-8}\%$, and low subsequent processing cost, thereby having a great application prospect. The nitrogen-doped carbon tubes after use can be regenerated and recovered, and its reutilization is still able to realize the complete transformation of adrenaline. The high utilization rate of catalytic material conforms to the concept of energy conservation, minimizing the costs.

6 Claims, 12 Drawing Sheets

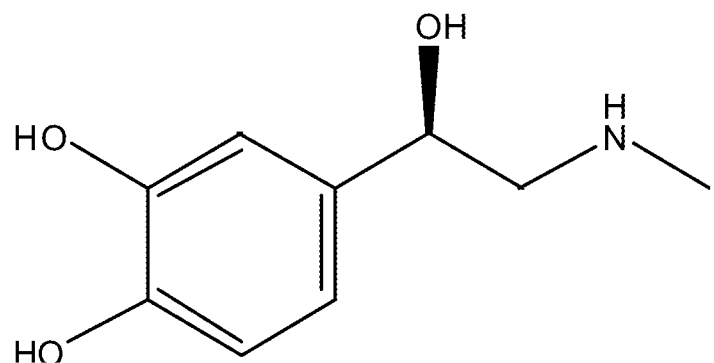
FIG. 1-a
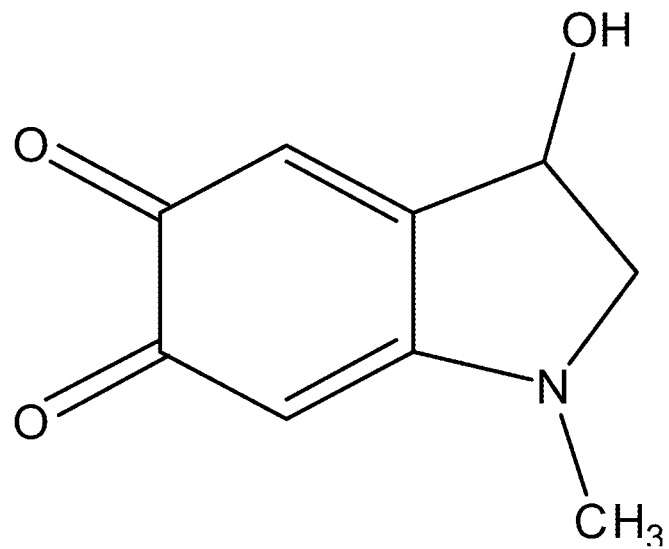
FIG. 1-b

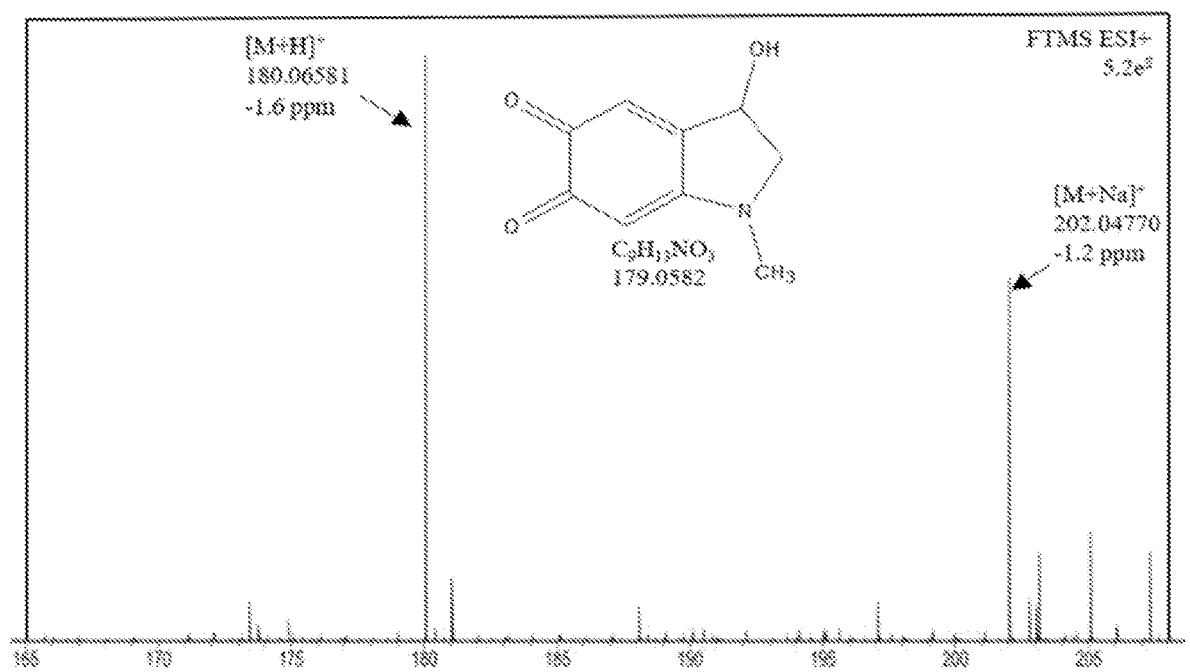
FIG. 4-a

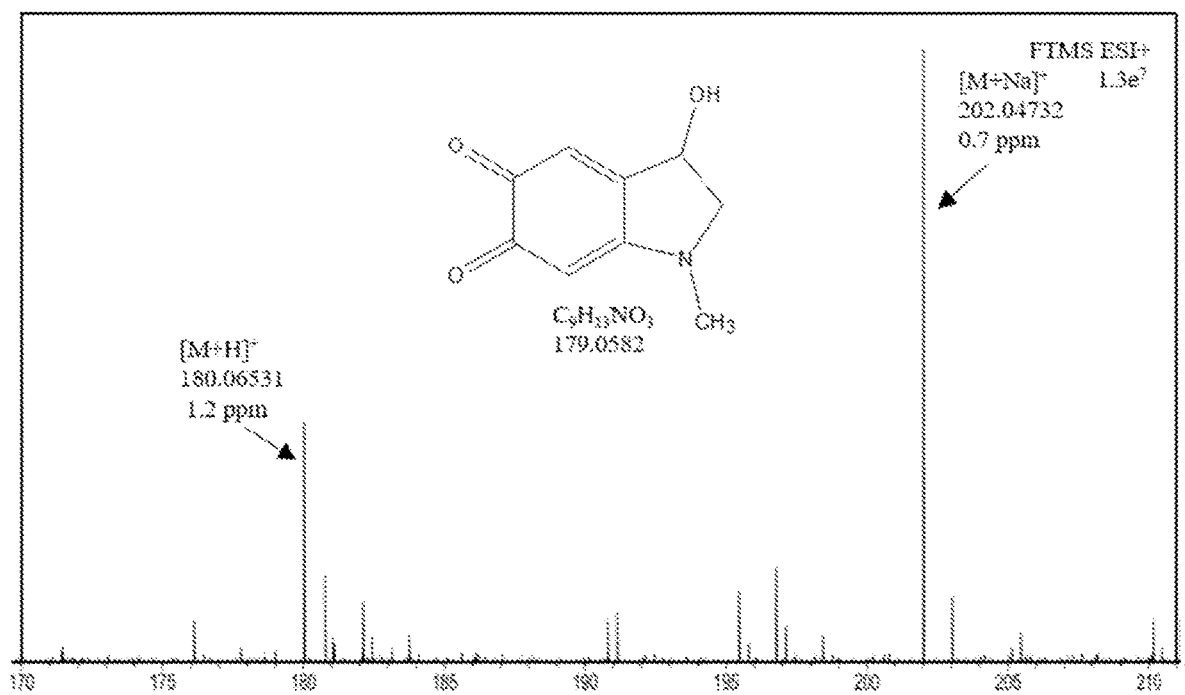
FIG. 4-b

METHOD FOR PREPARING ADRENOCHROME BY CATALYTIC OXIDATION USING NITROGEN-DOPED CARBON NANOTUBES

TECHNICAL FIELD

The invention belongs to the technical field of pharmaceutical preparation process, specifically relates to a method for preparing adrenochrome by catalytic oxidation using nitrogen-doped carbon nanotubes.

BACKGROUND

Adrenaline is an important catecholamine neurotransmitter and one of the stress hormones in the organisms, which can enhance contractibility of heart, increase response speed of nervous system, promote breakdown of liver glycogen and raise blood sugar, and play an important role in regulating physiological activities of cardiovascular system, nervous system, and endocrine system in human body, the structural formula of which is shown in FIG. 1-a. Adrenaline has a structure of catechol, which may be easily oxidized to generate an aminochrome adrenochrome which has a structure as shown in FIG. 1-b. Studies have indicated that adrenochrome has cardiotoxicity and neurotoxicity, and can inhibit the normal physiological functions of various enzymes in organisms. It is an intermediate that forms melanin in organisms. Therefore, adrenochrome is of great significance in clinical medicine and biological pharmaceutical.

As compared to adrenaline, adrenochrome is expensive, which has a price of up to 1568 RMB per 0.1 g in the current market while adrenaline has a price of only 163.2 RMB per 1 g. Accordingly, the development of a preparation method of adrenochrome has economic benefits. Currently, the method of preparing adrenochrome is mainly achieved by oxidation of adrenaline. The oxidation products are obtained by adding chemical oxidants and catalysts or an electrochemical method, but the productivity and purity of oxidation products is hard to balance. The currently used catalysts are mainly metal ions (e.g. $Cu^{2+}$) or natural enzymes, which are expensive and have unstable properties. Meanwhile, the addition of oxidants not only requires complex experimental conditions, but also increases costs and bring great difficulties to product purification, which is always accompanied by environmental pollution. The electrochemically catalytic oxidation method is significantly efficient, but requires high experimental equipment costs and complex operations.

SUMMARY

Provided is a preparation method for preparing adrenochrome by catalytic oxidation using nitrogen-doped carbon nanotubes, which realizes a high purity preparation of adrenochrome without adding foreign oxidants.

The solution is: a preparation method for preparing adrenochrome by catalytic oxidation using nitrogen-doped carbon nanotubes, which comprises the steps of:

S1: an appropriate amount of solid powder of nitrogen-doped carbon nanotubes with a nitrogen-doped amount of 1-5% is weighted and dispersed in a beaker containing ultrapure water, stirred on a magnetic stirring apparatus to give an uniform suspension of nitrogen-doped carbon nanotubes;

S2: a solid powder of adrenaline standards is dissolved in ultrapure water and ultrasonicated for 20 min to prepare an aqueous solution of adrenaline;

S3: the aqueous solution of adrenaline is added to the suspension of nitrogen-doped carbon nanotubes to keep a pH of 6-7 in the system and the reaction is stirred for 30-120 min with exclusion of light;

S4: the suspension is poured into a Buchner funnel after the end of reaction to perform vacuum filtration to give an aqueous solution of adrenochrome; the carbon tubes solid on filter paper are washed properly with methanol, suction-filtered, and the filtrate is combined;

S5: a PPL solid phase extraction cartridge is used, which is activated with methanol, ultrapure water and 0.01M HCl before use; the aqueous solution of adrenochrome obtained in S4 is passed through the PPL cartridge at an appropriate speed;

S6: After enrichment, the PPL cartridge is purified by an appropriate amount of ultrapure water; the PPL cartridge is then dried with pure $N_2$, and then slowly eluted with an appropriate amount of methanol immediately;

S7: The collected eluant is dried over anhydrous sodium sulfate and placed into a low-temperature bath to cool for 30 min at −30° C.; after crystal precipitation, the crystal is washed with methanol and placed in a freeze drier to give a adrenochrome solid which is stored at −20° C., protected from light and sealed;

S8: The method of claim 1, which is characterized in that: the suspension of nitrogen-doped carbon nanotubes formulated in S1 is added to an appropriate concentration of $H_2O_2$ aqueous solution and stirred uniformly.

As an aspect of the invention, the nitrogen-doped amount in solid powder of nitrogen-doped carbon nanotubes described in S1 is 1-5%. The experimental studies have found that the nitrogen-doped amount in the solid powder of nitrogen-doped carbon nanotubes has little impact on reaction. A nitrogen-doped amount above 1% can significantly promote the reaction to proceed, while the increase of nitrogen-doped amount after exceeding 5% has no significant effect on promotion.

As an aspect of the invention, to obtain a uniform suspension of carbon nanotubes in S1, an ultrasonication for 20-30 min under a condition of 30-50 W is performed. The ultrasonic frequency should not be too high to avoid breaking the carbon nanotubes.

As an aspect of the invention, the ultrasonic temperature of adrenaline in S2 should be kept below 25° C. since a high temperature is easy to cause decomposition of adrenaline. Hence, it is necessary to change water or add ice bag to lower temperature as appropriate for avoiding high temperature when ultrasonicated.

As an aspect of the invention, the temperature of catalytic oxidation reaction of adrenaline by nitrogen-doped carbon tubes in S3 is controlled at 25° C. by a magnetic stirring apparatus, which is consistent with room temperature. The reaction needs to continue for at least 30 min since a premature end of reaction will lead to an incomplete reaction of adrenaline, thereby to influence product purity. The pH of system needs to be kept at 6-7 since the pH will lead to instability of adrenochrome when too high while inhibit the progress of reaction when too low.

As an aspect of the invention, the residual carbon tubes on a filter paper in S4 should be collected and oven-dried at 80° C. for reutilization after washing.

As an aspect of the invention, the pre-treatment method of the PPL solid phase extraction cartridge in S5 is as follows: the cartridge is activated with methanol with a volume of 6 ml*2 firstly, then wetted with 6.0 ml*2 of ultrapure water and the residual methanol is washed off, and finally the filler is adjusted to an acidic environment with 6 mL*2 of 0.01M HCl, which is beneficial to the adsorption of adrenochrome. The flow rate of the aqueous solution of adrenochrome through the cartridge should not be higher than 2 mL/min to ensure a sufficient contact of adrenochrome with cartridge filler so as to improve enrichment efficiency.

As an aspect of the invention, the purification of the cartridge in S6 is by washing with ultrapure water with a volume of 6 mL*1, after drying with nitrogen, the cartridge is slowly eluted with 6 mL of methanol, in which the flow rate is controlled to 30 drops/min to ensure that the volume per minute through the cartridge is no more than 2 ml. Due to the limited adsorbability of the filler in each PPL cartridge, if the amount of aqueous solution to be enriched is high, the samples can be loaded to multiple PPL cartridges simultaneously and finally the eluants are combined.

The principle of the invention is as follows: the carbon nanotubes have good catalytic activity and electron transfer capability due to doping of nitrogen atom. They can activate adrenaline in an aqueous solution to loss its electrons and turn into an activated state, and transfer electrons to dissolved oxygen to form superoxide anions and $H_2O_2$, in which $H_2O_2$ is a main high-concentration active oxygen species, and the adrenaline in an activated state can be oxidized rapidly to adrenochrome. The generation of active oxygen stops when adrenaline in the system is degraded completely, and $H_2O_2$ in the system will be decomposed rapidly under a common action of nitrogen-doped carbon tubes and adrenochrome, which has no significant influence on product purity. The reaction course of oxidation from adrenaline to adrenochrome is as shown in FIG. 3.

As an improvement solution, $H_2O_2$ can be added to the preparation method of the invention to improve oxidation efficiency of adrenaline as a suspension of nitrogen-doped carbon tubes/$H_2O_2$ system. After addition of $H_2O_2$, the oxidation rate is increased significantly.

As compared to current techniques, the invention has several benefits as follows:
(1) The invention provides a novel preparation process of adrenochrome. By applying the solution of the invention, the addition of foreign oxidant is unnecessary. And the oxidation of adrenaline to adrenochrome can be realized by catalyzing dissolved oxygen using carbon nanomaterials which are cheap, have stable properties and can be recovered.
(2) The invention has a simple preparation process, mild reaction conditions, and cheap and available nitrogen-doped carbon tubes as catalyst. Additionally, the use of dissolved oxygen as oxidant makes it possible not to add additional oxidant to guarantee a maximum product purity and an impurity content below $10^{-8}$%, which avoids subsequent complex procedures of removing impurities and greatly saves costs, thereby having great application prospect.
(3) Nitrogen-doped carbon tubes have high catalytic efficiency, and can completely transform adrenaline into adrenochrome within 30 minutes, which guarantees both high yield and high purity, no by-products, and no pollution to the environment.
(4) The nitrogen-doped carbon tubes after use can be regenerated and recovered, and its reutilization is still able to realize the complete transformation of adrenaline. The high utilization rate of catalytic material conforms to the concept of energy conservation, minimizing the costs.

BRIEF DESCRIPTION OF THE DRAWINGS

FIGS. 1-a and 1-b show the structural formula of adrenaline and adrenochrome, in which a is the structural formula of adrenaline and b is the structural formula of adrenochrome;
FIGS. 4-a and 4-b show a comparison of Fourier high-resolution mass spectrums of the product of the invention and an adrenochrome standard, in which a is the mass spectrum of the product of the invention, and b is the mass spectrum of an adrenochrome standard.

DESCRIPTION OF THE EMBODIMENTS

Example 1

Figure 2:
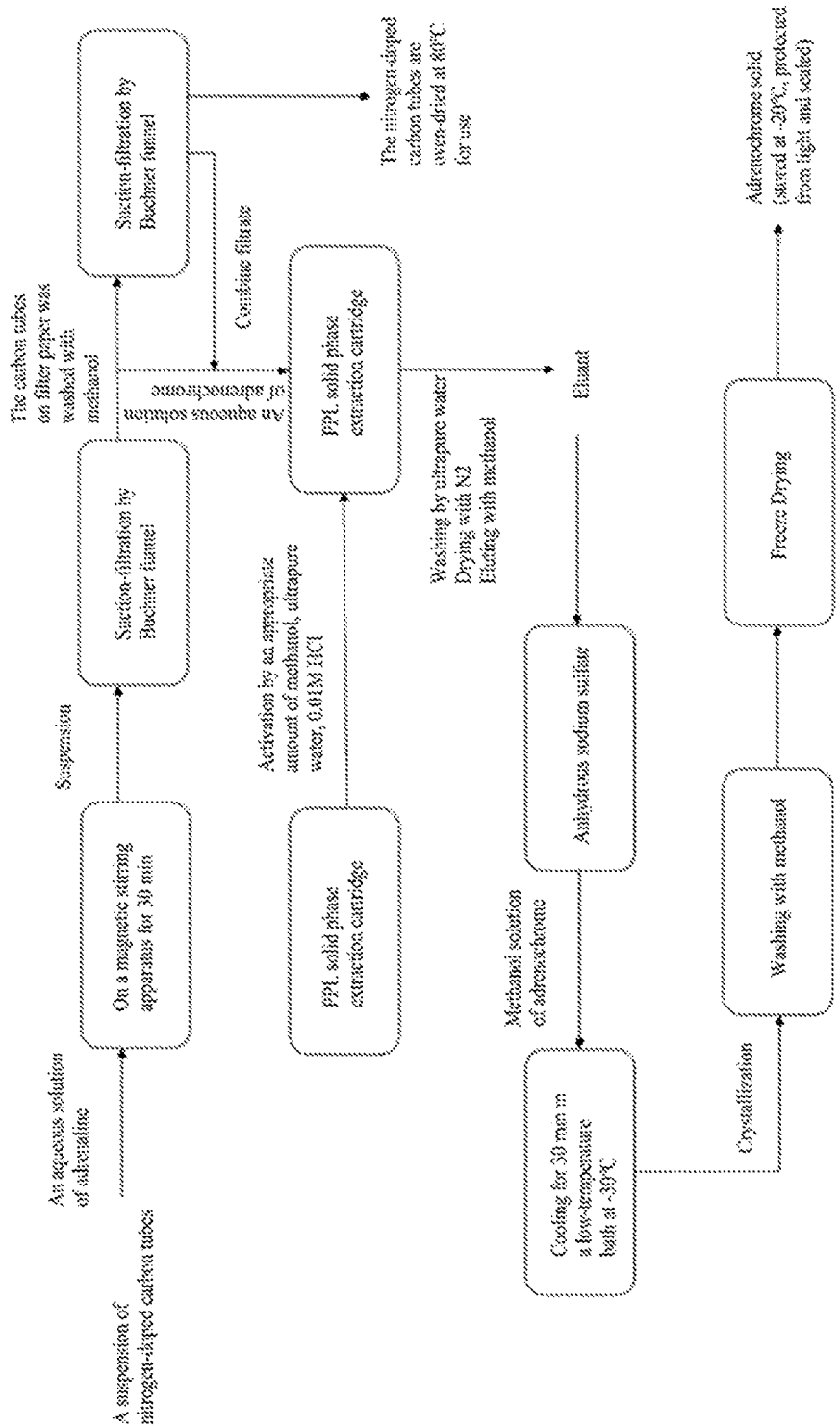
FIG. 2 is a flow chart of preparation process of the invention.
Figure 3:
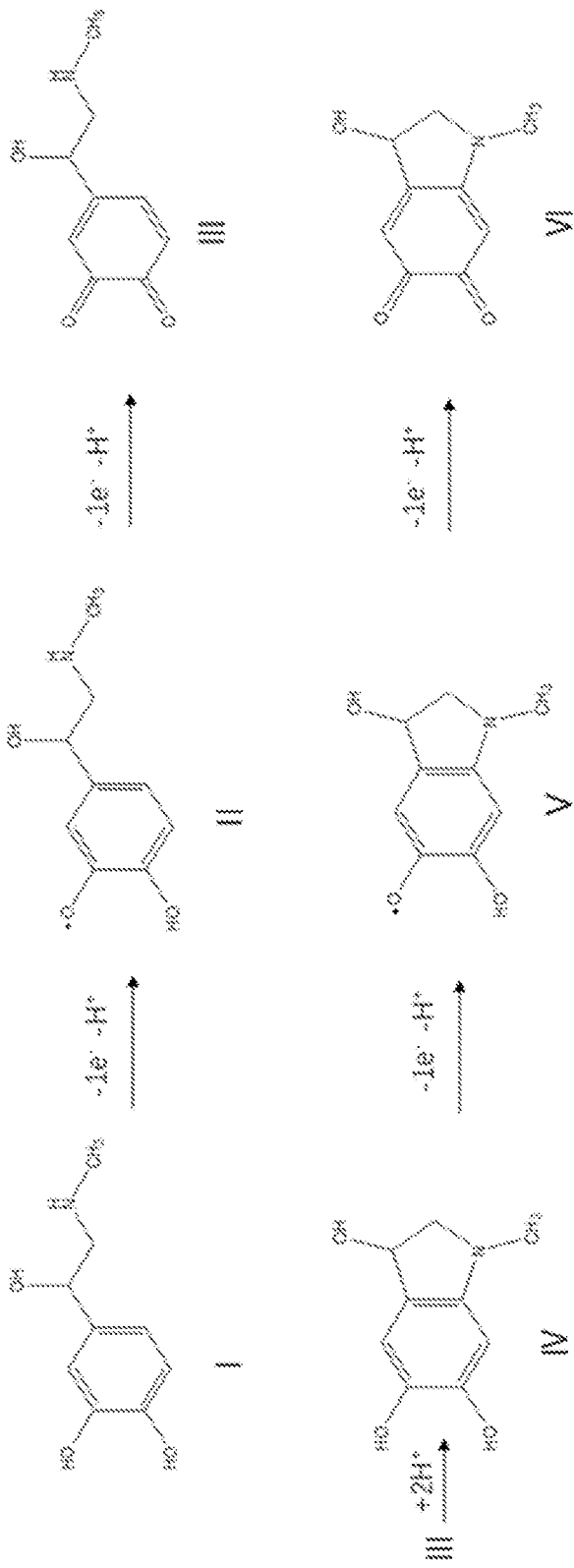
FIG. 3 is a reaction course of oxidation of adrenaline to adrenochrome, in which I: Adrenaline; II: Adrenaline semiquinone; III: Adrenaline quinone; IV: Leucoadrenochrome; V: Leucoadrenochrome semiquinone; VI: Adrenochrom.

The example illustrates by example of a preparation method for preparing adrenochrome by catalytic oxidation using nitrogen-doped carbon nanotubes, as shown in FIG. 2, the method comprises the steps of:
S1: 30 mg of solid powder of nitrogen-doped carbon nanotubes with an nitrogen-doped amount of 3.19% is weighted and dispersed in a beaker containing 190 mL of ultrapure water, ultrasonicated for 20 min under a condition of 50 W, constantly stirred on a magnetic stirring apparatus for 2 h at 200 rpm and 25° C. to give an uniform suspension of nitrogen-doped carbon nanotubes;
S2: 16 mg of a solid powder of adrenaline standards is dissolved in 20 mL of ultrapure water and ultrasonicated for 20 min at 20° C. to prepare an aqueous solution of epinephrine with a concentration of 800 mg/L;
S3: 10 mL of adrenaline solution is sucked out and added to the suspension of nitrogen-doped carbon nanotubes by a pipetting gun to keep a pH of 6 in the system at 25° C. and the reaction is stirred for 30 min with exclusion of light;
S4: the suspension is poured into a Buchner funnel after the end of reaction to perform vacuum filtration to give an aqueous solution of adrenochrome; the carbon tube solid on filter paper is washed properly with methanol, suction-filtered, and the filtrate is combined;
S5: PPL solid phase extraction cartridge is activated with methanol with a volume of 6 ml*2 firstly, then wetted with 6.0 ml*2 of ultrapure water and the residual methanol is washed off, and finally the filler is adjusted to an acidic environment with 6 mL*2 of 0.01M HCl; after activation, the aqueous solution of adrenochrome obtained in S4 is passed through the PPL cartridge at a speed of 2 mL/min.
S6: After enrichment, the PPL cartridge is purified by washing with ultrapure water with a volume of 6 mL*1; then the PPL cartridge is dried with clean $N_2$, and is slowly eluted with 6 mL of methanol immediately, in which the flow rate is controlled to 30 drops/min to ensure that the volume per minute through the cartridge is no more than 2 ml.
S7: The collected eluant is dried over anhydrous sodium sulfate and placed into a low-temperature bath to cool for 30 min at −30° C.; after crystal precipitation, the crystal is washed with methanol and placed in a freeze drier to give a adrenochrome solid which is stored at −20° C., protected from light and sealed.

Figure 5:
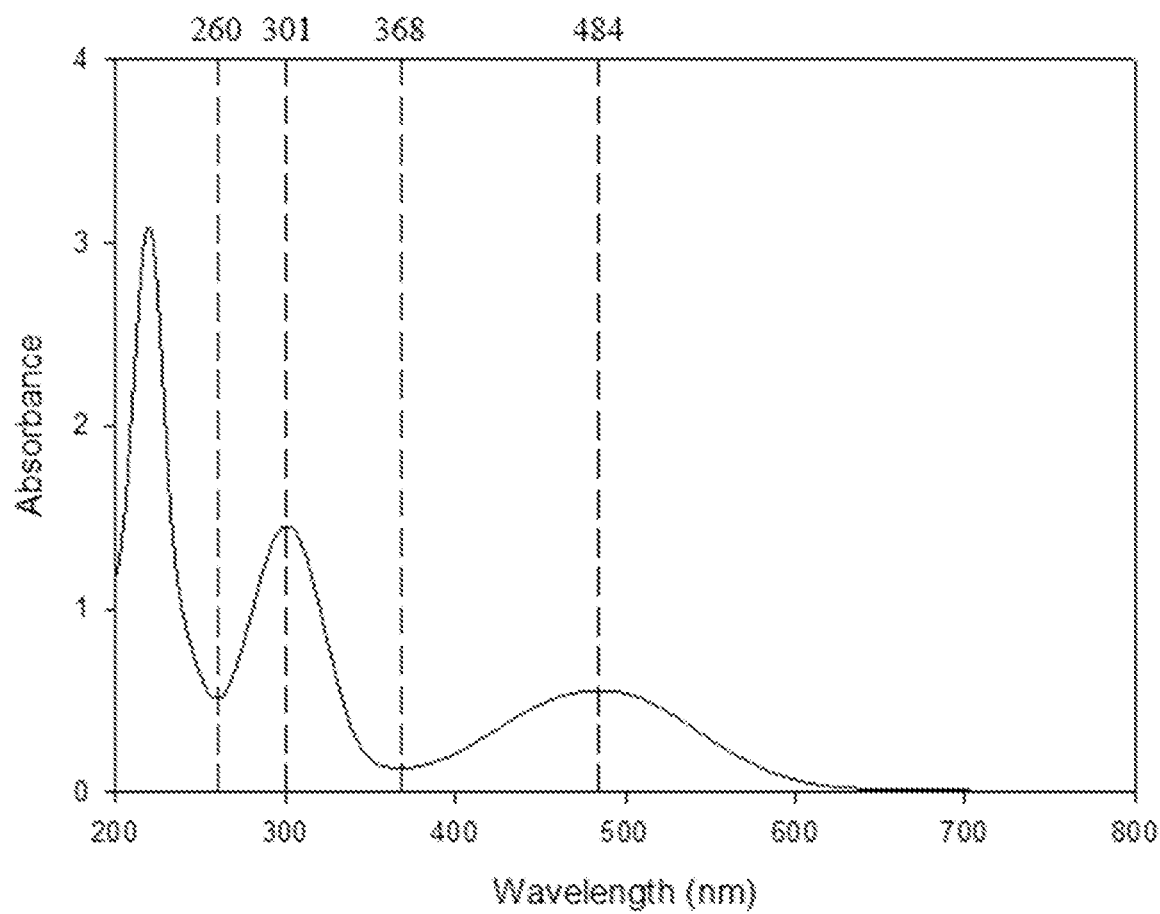
FIG. 5 is an ultraviolet spectrum of the product of the invention.

FIG. 4 is a comparison of Fourier high-resolution mass spectrums of the product prepared by this example and an adrenochrome standard, in which a is the mass spectrum of the product of the invention, and b is the mass spectrum of an adrenochrome standard. As seen from the FIGS. 4-a and 4-b, the mass spectrum of the product is almost identical to that of the standard and there is no impure peak, indicating that the product is unique and of high purity;

FIG. 5 is an ultraviolet spectrum of the product prepared by this example. As seen from the FIG. 5, the sample presents two maximum absorption peaks at 301 nm and 484 nm, and two minimum absorption peaks at 260 nm and 368 nm in UV absorption curve, which are characteristic absorption peaks of adrenochrome. Given that there are no other peaks in UV spectrum and according to detection limit of the spectrophotography, it can be judged that the impurity content of the product is lower than $10^{-8}$%.

Example 2

The catalytic oxidation ability of different kinds of carbon nanomaterials to adrenaline were compared.

The difference from example 1 is that: the nitrogen-doped carbon nanotubes were replaced with common carbon nanotubes, graphite, and graphene oxide of the same mass in S1, and the remaining process steps and parameters are the same as those of example 1. The concentration of adrenaline in the system at different times was determined by liquid chromatography to evaluate the catalytic oxidation performance of the materials.

The specific steps of sampling are as follows: 0.5 mL of the reaction suspension was sucked at a certain time interval and added by a pipetting gun to a chromatographic vial filled with 0.5 mL of methanol to be determined for realizing the purpose of extracting the adrenaline in solution state and carbon nanotube-adsorption state.

Figure 6:
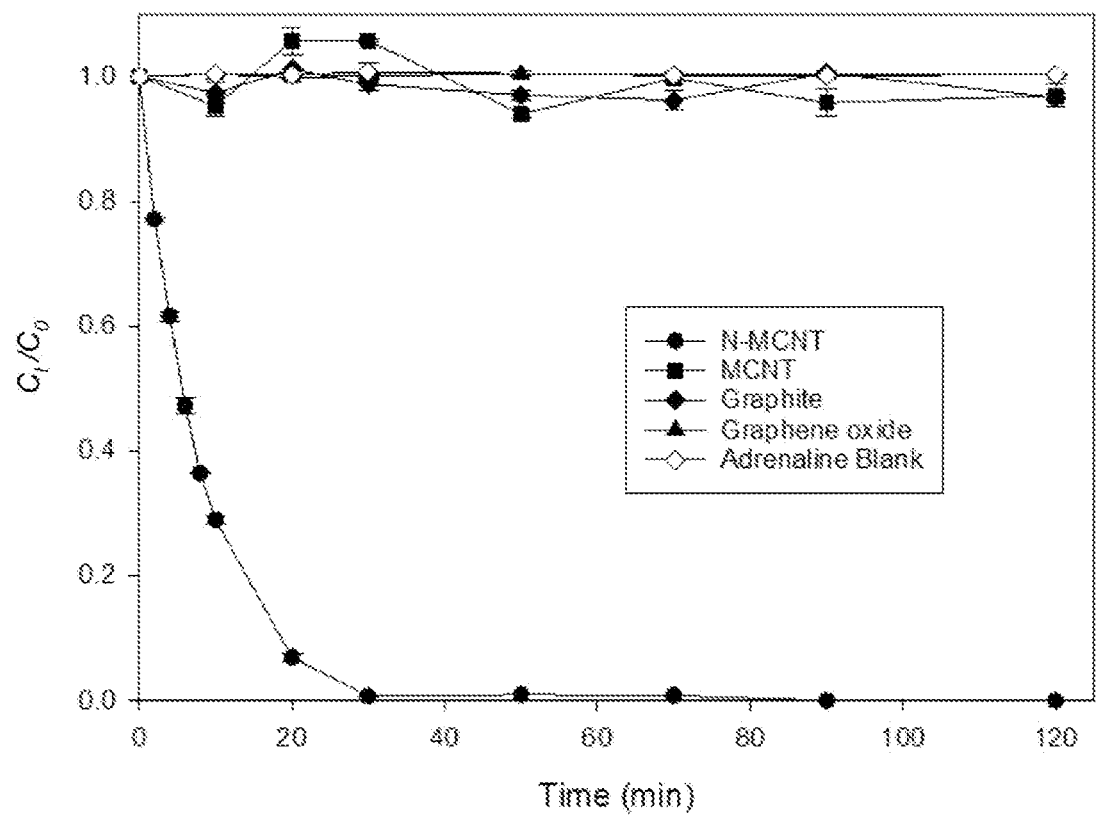
FIG. 6 is a comparison of the catalytic oxidation ability of different kinds of carbon nanomaterials to adrenaline.

The detection conditions of liquid chromatography are as follows: the detector is a high-performance liquid chromatography (Agilent 1200) tandem fluorescence detector, using a 4.6×150 mm SB-C18 chromatography column (Agilent), with a mobile phase of 0.02M potassium dihydrogen phosphate (pH 4-5):methanol (v:v)=98:2, an excitation wavelength of 316 nm, an emission wavelength of 280 nm, a flow rate of 1 mL/min, and an injection volume of 10 μL. The data is as shown in FIG. 6.

The conclusion is that among common carbon nanomaterials, only nitrogen-doped carbon nanotubes can catalyze the oxidation of adrenaline to adrenochrome.

Example 3

The effect of dissolved oxygen on the catalytic oxidation of adrenaline was studied.

Figure 7:
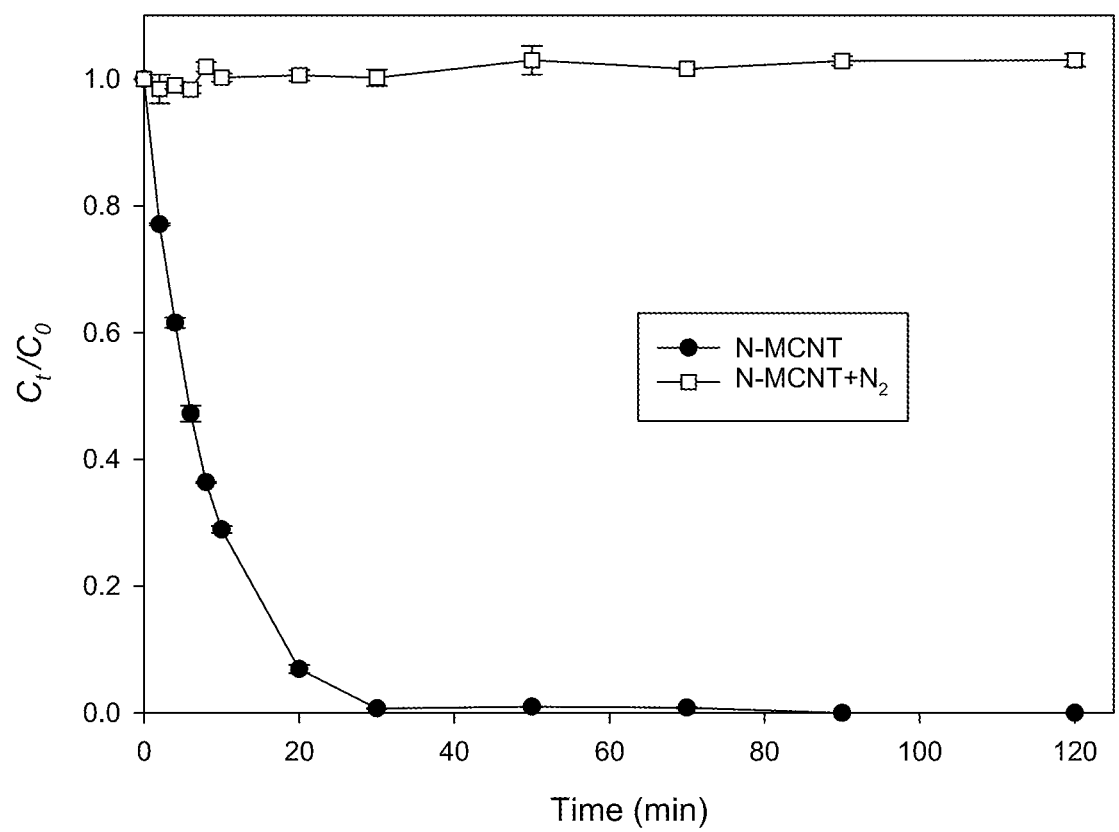
FIG. 7 is a comparison of effect of dissolved oxygen on the catalytic oxidation of adrenaline.

The difference from example 1 is that in S1 and S2, the ultrapure water used to formulated the suspension of nitrogen-doped carbon nanotubes and the aqueous solution of adrenaline was purged with high-purity nitrogen (99.999%) previously to remove dissolved oxygen, the remaining process steps and parameters are the same as those of example 1. The concentration change of epinephrine at different times was determined by using liquid chromatography to evaluate influence of the presence and absence of dissolved oxygen on catalytic oxidation of nitrogen-doped carbon tubes to adrenaline, and the data is as shown in FIG. 7.

The conclusion is that dissolved oxygen is a necessary condition for catalytic oxidation of adrenaline, and the production of anaerobic environment must be avoided during the reaction.

Example 4

The effect of the pH of the reaction system on the catalytic oxidation efficiency to adrenaline was studied.

Figure 8:
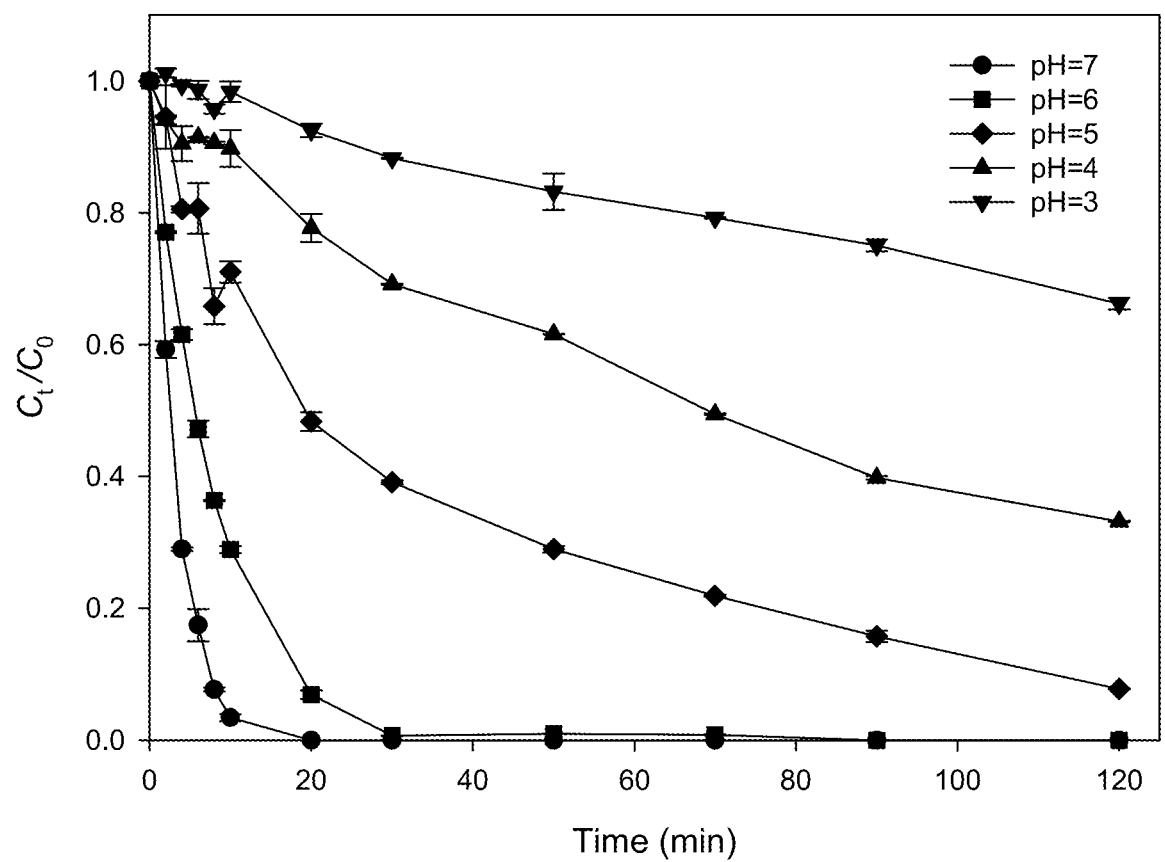
FIG. 8 is a result graph showing the effect of the pH of the reaction system on the catalytic oxidation efficiency to adrenaline.

The difference from example 1 is that five pH values of 3, 4, 5, 6, and 7 were set, and the remaining process steps and parameters are the same as those of example 1. The concentration change of adrenaline at different times was determined by using liquid chromatography to explore the influence of pH on reaction and the optimum pH of the reaction, and the results are as shown in FIG. 8.

The conclusion is that high pH can promote the oxidation of adrenaline, while low pH can inhibit the progress of the reaction.

It can be seen from the experimental data that increasing the pH from 6 to 7 has no obvious effect on promoting the reaction. In addition, adrenochrome is unstable under high pH conditions, so it is best to keep the system pH at 6.

Example 5

The effect of the reaction temperature of the system on the catalytic oxidation efficiency to adrenaline was studied.

Figure 9:
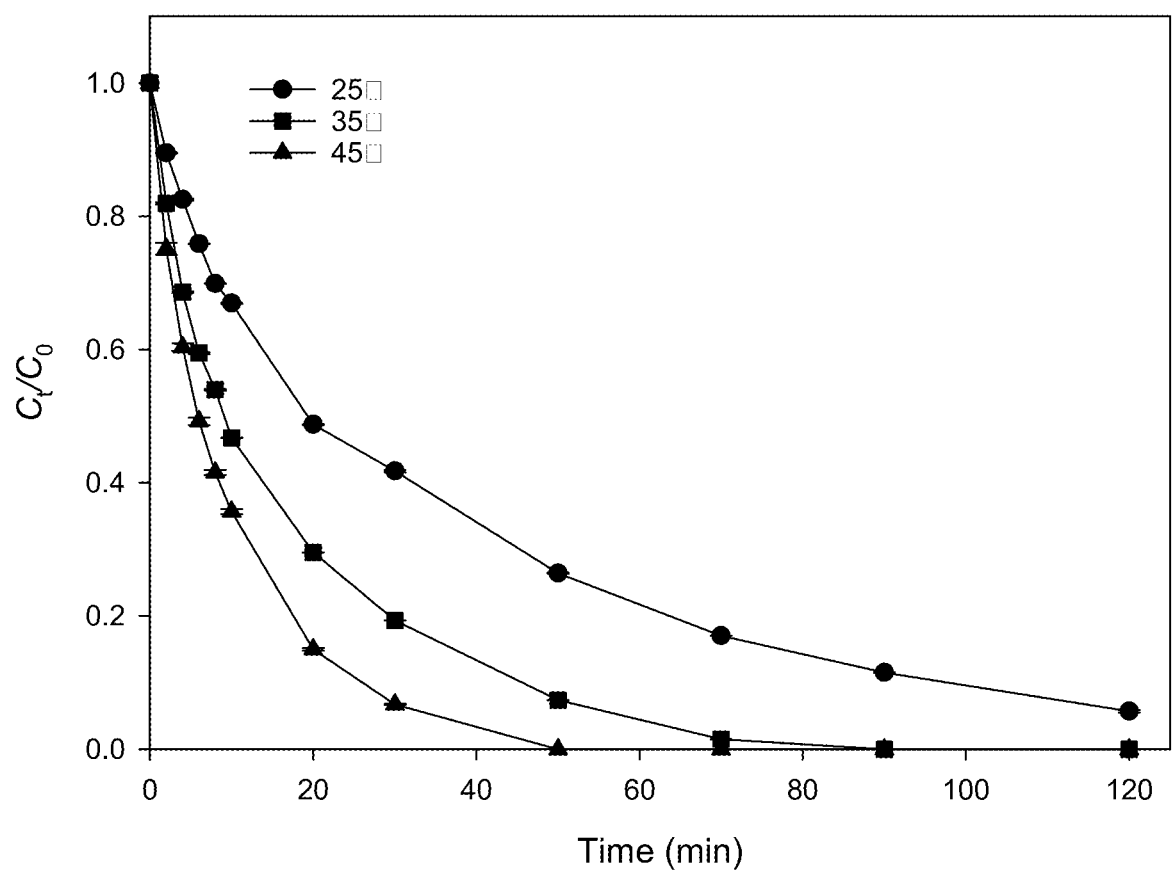
FIG. 9 is a comparison of the effect of the temperature of the reaction system on the catalytic oxidation efficiency to adrenaline.

The difference from example 1 is that the reaction condition of example 1 is 25 degrees Celsius. To better explore the effect of temperature on the reaction, the dose of nitrogen-doped carbon tubes was changed from 30 mg to 10 mg, and three temperature gradients of 25° C., 35° C. and 45° C. were set. The remaining process steps and parameters are the same as those of example 1. The concentration change of adrenaline at different times was determined by using liquid chromatography to explore the optimum reaction temperature of the system. And the results are as shown in FIG. 9.

The conclusion is that the increase of temperature of the system is helpful to accelerate the reaction rate, so it can be appropriately heated during the reaction.

Given that adrenochrome is unstable and easily decomposed at high temperature, it is best to keep the reaction temperature of the system at 25° C.

Example 6

The effect of the recovered and regenerated carbon tubes nitrogen-doped carbon tubes on the products was studied.

Figure 10:
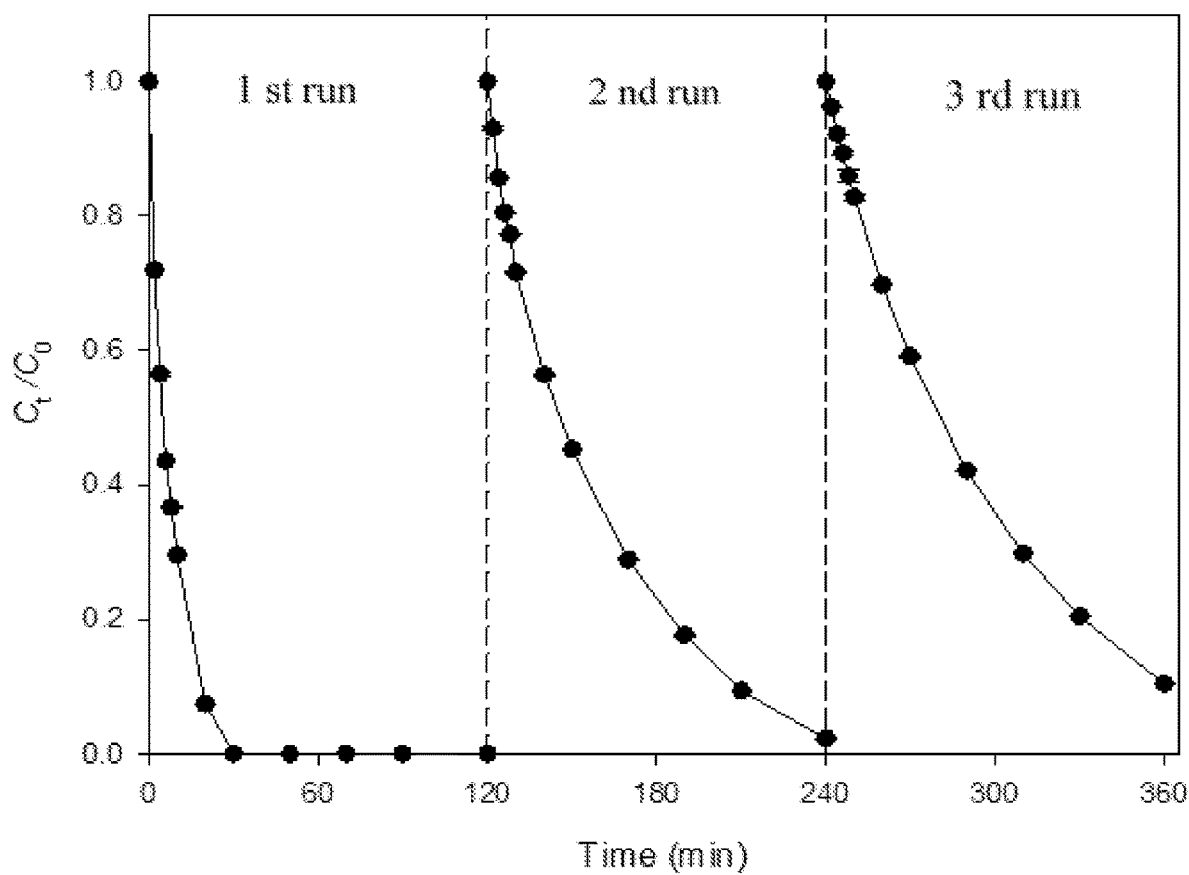
FIG. 10 is a result graph showing the effect of the recovered and regenerated carbon tubes nitrogen-doped carbon tubes on the products.

The difference from example 1 is that the nitrogen-doped carbon tubes used are recovered nitrogen-doped carbon tubes that have been used once, twice, and three times, and the remaining process steps and parameters are the same as those of example 1. The concentration change of adrenaline at different times was determined by using liquid chromatography to explore recycling capacity of nitrogen-doped carbon nanotubes, and the results are as shown in FIG. 10.

The conclusion is that the nitrogen-doped carbon tubes after use can be regenerated and recovered, and its reutilization is still able to realize the complete transformation of epinephrine.

Example 7

The effect of $H_2O_2$ addition on the catalytic oxidation of epinephrine by nitrogen-doped carbon nanotubes was studied.

Figure 11:
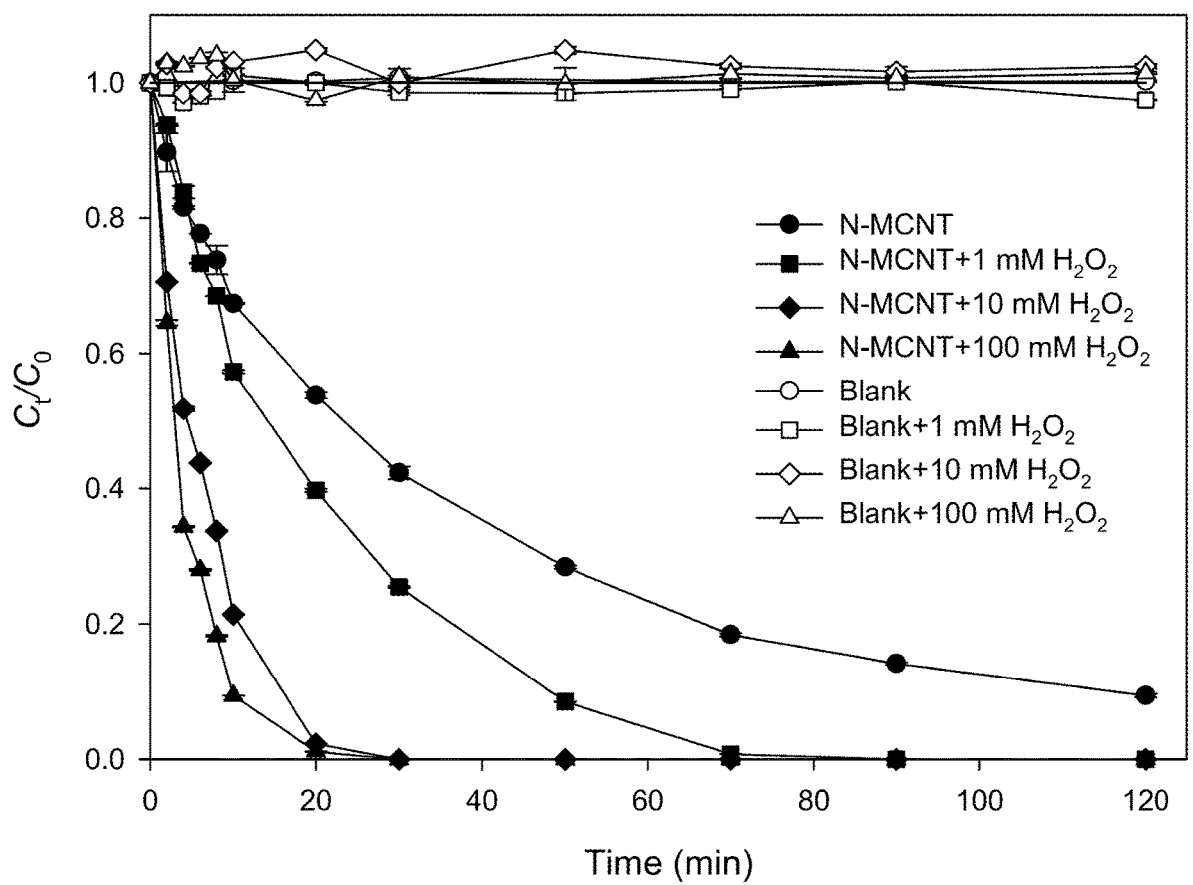
FIG. 11 is a result graph showing the effect of different concentrations of $H_2O_2$ on the catalytic oxidation efficiency to adrenaline.

The difference from Example 1 is that the dose of nitrogen-doped carbon nanotubes was changed from 30 mg to 10 mg, and 1 mM, 10 mM, and 100 mM of aqueous solutions were added at the same time. The remaining process steps and parameters are the same as those of example 1. As a blank control, was added to the aqueous solution of adrenaline. The concentration change of adrenaline at different times was determined by using liquid chromatography, and the results are as shown in FIG. 11.

The conclusion is that adrenaline cannot be oxidized by $H_2O_2$ without activation by addition of nitrogen-doped carbon nanotubes. In the presence of nitrogen-doped carbon nanotubes, the addition of $H_2O_2$ can significantly increase the oxidation rate of adrenaline.

When the $H_2O_2$ concentration is increased from 10 mM to 100 mM, the effect on the reaction rate is not significant, so 10 mM can be selected as the optimal concentration of $H_2O_2$.

However, the excess in the system will increase the difficulty of subsequent purification steps, which will affect the product purity.

What is claimed is:

1. A method for preparing adrenochrome by catalytic oxidation using nitrogen-doped carbon nanotubes, which is characterized in that the method comprises the steps of:
    S1: an appropriate amount of solid powder of nitrogen-doped carbon nanotubes is weighted and dispersed in a beaker containing ultrapure water, stirred on a magnetic stirring apparatus to give a uniform suspension of nitrogen-doped carbon nanotubes;
    S2: a solid powder of adrenaline standards is dissolved in ultrapure water and ultrasonicated for 20 min to prepare an aqueous solution of adrenaline;
    S3: the aqueous solution of adrenaline is added to the suspension of nitrogen-doped carbon nanotubes to keep a pH of 6-7 in the system and the reaction is stirred for 30-120 min with exclusion of light;
    S4: the suspension is poured into a Buchner funnel after the end of reaction to perform vacuum filtration to give an aqueous solution of adrenochrome; the carbon tube solid on filter paper is washed appropriately with methanol, suction-filtered, and the filtrates are combined;
    S5: a PPL solid phase extraction cartridge is used, which is activated with methanol, ultrapure water and 0.01M HCl before use; the aqueous solution of adrenochrome obtained in S4 is passed through the PPL cartridge at an appropriate speed;
    S6: After enrichment, the PPL cartridge is purified by an appropriate amount of ultrapure water; the PPL cartridge is then dried with pure N2, and then slowly eluted with an appropriate amount of methanol immediately;
    S7: The collected eluant is dried over anhydrous sodium sulfate and placed into a low-temperature bath to cool for 30 min at −30° C.; after crystal precipitation, the crystal is washed with methanol and placed in a freeze drier to give a adrenochrome solid which is stored at −20° C., protected from light and sealed.

2. The method of claim 1, which is characterized in that: the doped amount of the solid powder of nitrogen-doped carbon nanotubes described in S1 is 1-5%.

3. The method of claim 1, which is characterized in that: to obtain a uniform suspension of carbon nanotubes in S1, an ultrasonication for 20-30 min under a condition of 30-50 W is performed.

4. The method of claim 1, which is characterized in that: the pre-treatment method of the PPL solid phase extraction cartridge in S5 is as follows: the cartridge is activated with methanol with a volume of 6 ml*2 firstly, then wetted with 6.0 ml *2 of ultrapure water and the residual methanol is washed off, and finally the filler is adjusted to an acidic environment with 6 mL*2 of 0.01M HCl, and the flow rate of the aqueous solution of adrenochrome through the cartridge should not be higher than 2 mL/min.

5. The method of claim 1, which is characterized in that: the purification of the cartridge in S6 is by washing with ultrapure water with a volume of 6 mL*1, after drying with nitrogen, the cartridge is slowly eluted with 6 mL of methanol, in which the flow rate is controlled to 30 drops/min to ensure that the volume per minute through the cartridge is no more than 2 ml; due to the limited adsorbability of the filler in each PPL cartridge, if the amount of aqueous solution to be enriched is high, the samples can be loaded to multiple PPL cartridges simultaneously and finally the eluants are combined.

6. The method of claim 1, which is characterized in that: the suspension of nitrogen-doped carbon nanotubes formulated in S1 is added to an appropriate concentration of $H_2O_2$ aqueous solution and stirred uniformly.

* * * * *